(12) United States Patent
Kobayashi et al.

(10) Patent No.: US 7,025,782 B2
(45) Date of Patent: Apr. 11, 2006

(54) INSERTION DEVICE FOR DEFORMABLE INTRAOCULAR LENS

(75) Inventors: Kenichi Kobayashi, Tokyo (JP);
Toshikazu Kikuchi, Hachioji (JP);
Hidenori Yoshida, Funabashi (JP)

(73) Assignee: Canon-Staar Co., Inc., Tokyo (JP)

( * ) Notice: Subject to any disclaimer, the term of this patent is extended or adjusted under 35 U.S.C. 154(b) by 214 days.

(21) Appl. No.: 10/227,786

(22) Filed: Aug. 26, 2002

(65) Prior Publication Data

US 2003/0045886 A1   Mar. 6, 2003

(30) Foreign Application Priority Data

Sep. 4, 2001   (JP) .............................. 2001-267398

(51) Int. Cl.
*A61F 2/16* (2006.01)
(52) U.S. Cl. ..................... 623/6.12; 623/6.11; 606/107
(58) Field of Classification Search ................ 623/4.1, 623/6.11–6.62; 606/107; 604/164.01, 264
See application file for complete search history.

(56) References Cited

U.S. PATENT DOCUMENTS

| | | | | |
|---|---|---|---|---|
| 4,699,140 | A * | 10/1987 | Holmes et al. | 606/107 |
| 4,834,094 | A * | 5/1989 | Patton et al. | 606/107 |
| 4,919,130 | A * | 4/1990 | Stoy et al. | 606/107 |
| 5,123,905 | A * | 6/1992 | Kelman | 606/107 |
| 5,190,552 | A * | 3/1993 | Kelman | 606/107 |
| 6,214,015 | B1 * | 4/2001 | Reich et al. | 606/107 |
| 6,241,737 | B1 * | 6/2001 | Feingold | 606/107 |
| 6,447,520 | B1 * | 9/2002 | Ott et al. | 606/107 |
| 6,471,708 | B1 * | 10/2002 | Green | 606/107 |
| 6,497,708 | B1 * | 12/2002 | Cumming | 606/107 |

* cited by examiner

*Primary Examiner*—Glenn K. Dawson
(74) *Attorney, Agent, or Firm*—Roth & Goldman, P.A.

(57) ABSTRACT

In an insertion device for deforming a deformable intraocular lens to a smaller size and inserting the intraocular lens into an eye via an insertion tube, a slit is formed in an insertion end portion of the insertion tube, and cut surfaces of the slit and at least the inner wall surface of the insertion end portion are connected by curved surfaces.

1 Claim, 11 Drawing Sheets

INSERTION DEVICE FOR DEFORMABLE INTRAOCULAR LENS

BACKGROUND OF THE INVENTION

1. Field of the Invention

The present invention relates to an insertion device for a deformable intraocular lens that is inserted into the eye in place of the natural lens when the latter is physically extracted because of cataracts.

2. Description of the Related Art

Conventionally, many types of such intraocular-lens insertion devices have been proposed.

When an intraocular lens having coil-shaped supports is inserted into the eye by use of an intraocular-lens insertion device, the intraocular lens may be abruptly ejected from an open end of an insertion end portion of the insertion device due to elastic restoration force of the intraocular lens. In order to mitigate the problem of such abrupt ejection, the assignee of the present invention has proposed an improved insertion device capable of controlling the final insertion speed at which an intraocular lens is inserted in the eye (Japanese Patent Application Laid-Open (kokai) No. 08-038542).

That is, in the insertion device disclosed in Japanese Patent Application Laid-Open No. 08-038542, a slit is formed in the insertion end portion made of elastically deformable plastic. Immediately before a folded intraocular lens is ejected from the open end of the insertion end portion of the insertion device and is allowed to restore its predetermined original shape, the slit allows a portion of the intraocular lens to project outside therethrough in order to partially absorb elastic restoration force. In addition, cut surfaces located above and below the slit come into contact with portions of opposite faces of the intraocular lens and nip the intraocular lens, to thereby prevent abrupt ejection of the intraocular lens from the open end of the insertion end portion by means of frictional force.

Figure 13:
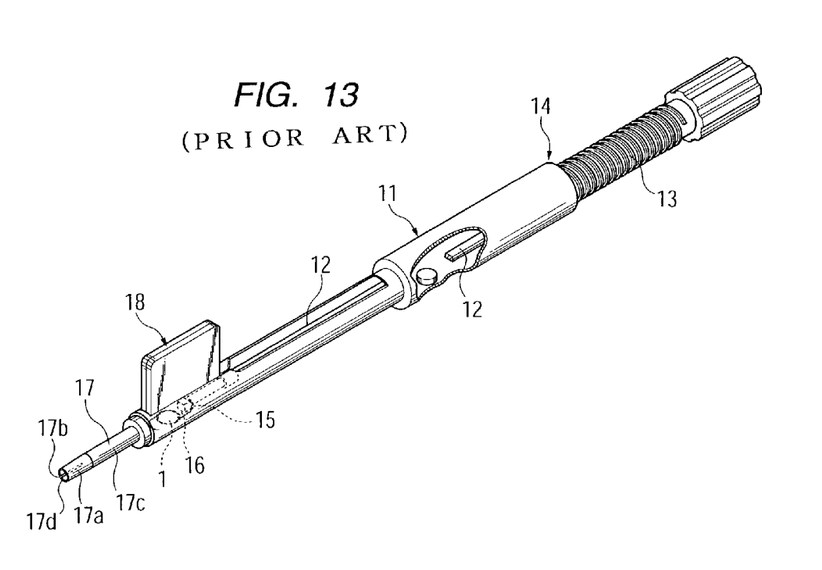
FIG. 13 is a partially cutaway perspective view of a conventional intraocular-lens insertion device.
Figure 14:
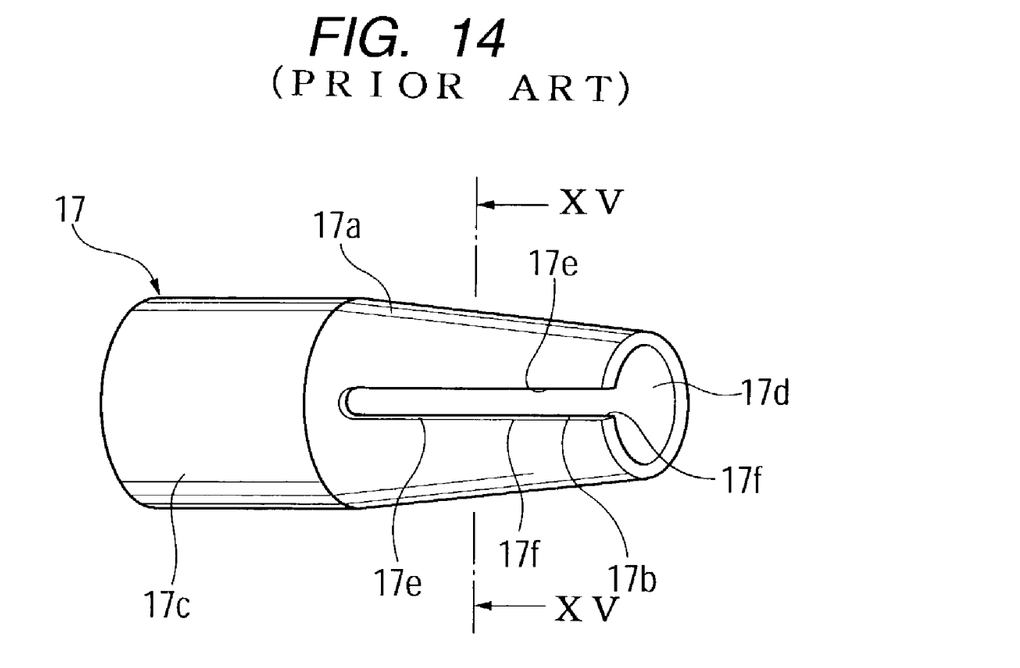
FIG. 14 is an enlarged perspective view of the insertion end portion of the conventional intraocular-lens insertion device.
Figure 15:
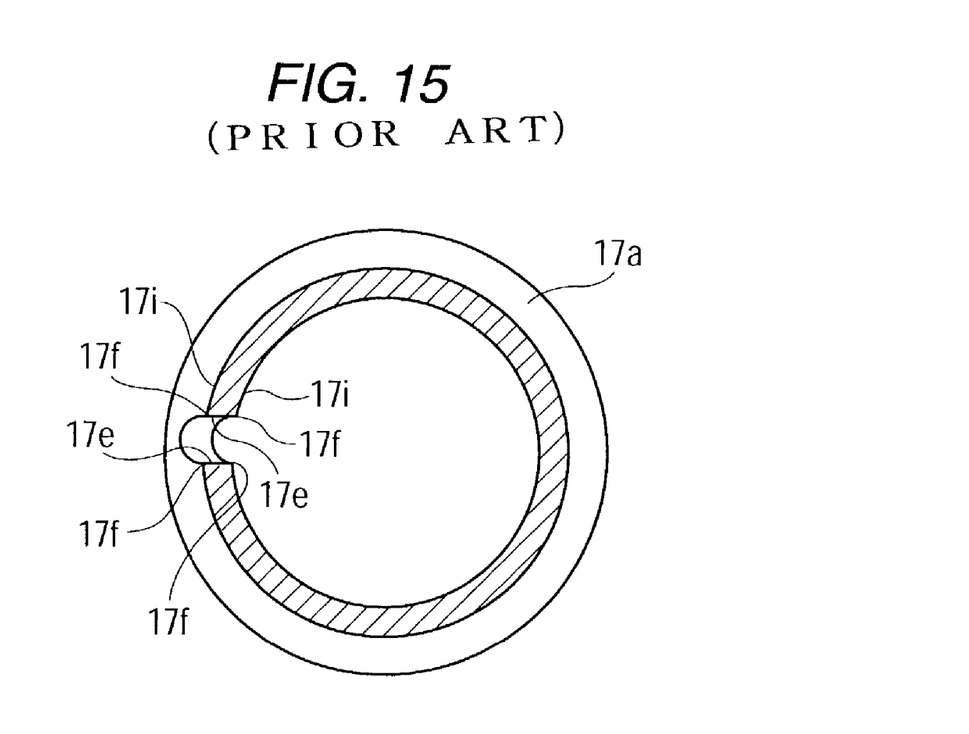
FIG. 15 is a cross sectional view taken along line XV—XV of FIG. 14.
Figure 16:
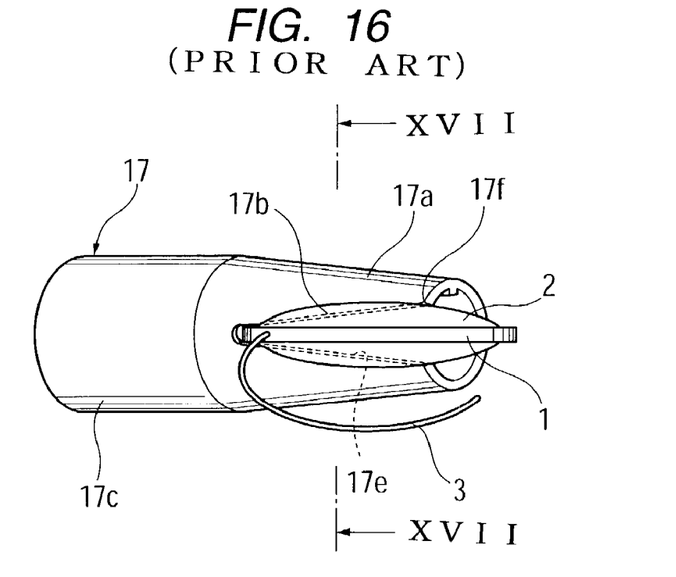
FIG. 16 is an enlarged perspective view of the insertion end portion of the conventional intraocular-lens insertion device in a used sate.
Figure 17:
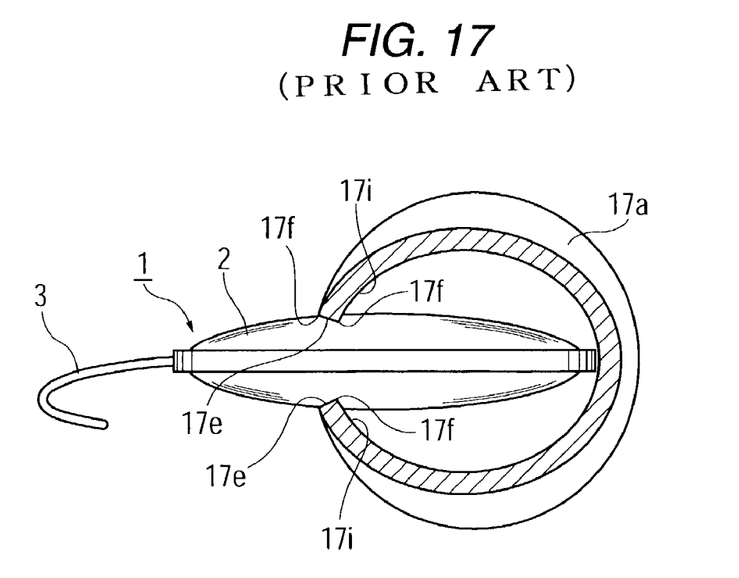
FIG. 17 is a cross sectional view taken along line XVII—XVII of FIG. 16.

Such a convention insertion device for a deformable intraocular lens will be described with reference to FIGS. 13 to 17. FIG. 13 is a partially cutaway perspective view of a conventional insertion device for a deformable intraocular-lens. FIG. 14 is an enlarged perspective view of the insertion end portion of the insertion device. FIG. 15 is a cross sectional view taken along line XV—XV of FIG. 14. FIG. 16 is an enlarged perspective view of the insertion end portion of the insertion device which is used for description of operation. FIG. 17 is a cross sectional view taken along line XVII—XVII of FIG. 16.

In FIG. 13, reference numeral 11 denotes a device body; 12 denotes a push rod; 13 denotes a male-thread shaft; and 14 denotes a push-out mechanism.

Reference numeral 18 denotes an enclosing member. The enclosing member 18 is provided with a lens receiving section 16 having a hinge portion 15. An insertion tube 17 projects from the front end of the lens receiving section 16. A tapered insertion end portion 17a of the insertion tube 17 has an axially extending slit 17b. The slit 17b has a length shorter than a portion of the tapered insertion end portion 17a which is to be inserted into the eye through an incision formed thereon.

The slit 17b has a constant width slightly smaller than the thickness of an optical portion 2 of an intraocular lens. For example, when the optical portion 2 has a thickness of 1 mm, the width of the slit 17b is set to 0.9 mm. Reference numeral 17c denotes a base end portion of the insertion tube 17, and 17d denotes an open end.

The conventional insertion device having the above-described structure is used as follows. The intraocular lens 1 is placed on the lens receiving section 16 of the enclosing member 18 and is folded into a smaller size before being loaded onto the insertion device body.

Upon completion of loading of the intraocular lens 1, the male-thread shaft 13 of the intraocular-lens insertion device is rotated in order to screw-feed the push rod 12. As a result, a process of inserting the intraocular lens into the eye starts. Behavior of the insertion end portion 17a of the insertion tube 17 during the above described insertion of the intraocular lens into the eye will be described with reference to FIGS. 16 and 17.

The intraocular lens 1 is gradually pushed forward by the tip end of the push rod 12. When the intraocular lens 1 reaches the tapered insertion end portion 17a of the insertion tube 17, as shown in FIG. 17, the axially extending slit 17b of the insertion end portion 17a opens gradually. As a result, stresses in the optical portion 2 of the intraocular lens 1, which has been folded at the base end portion 17c of the insertion tube 17, are gradually released at the insertion end portion 17a. Subsequently, the intraocular lens 1 is inserted into the eye from the open end 17d.

As shown in FIG. 17, the slit 17b holds the optical portion 2 of the intraocular lens 1 while sandwiching it, to thereby prevent abrupt ejection of the intraocular lens 1 into the eye. In addition, although the slit 17b releases stresses from the intraocular lens 1, the intraocular lens 1 is retained at the insertion end portion 17a, because cut surfaces located above and below the slit 17b hold the intraocular lens 1 from both sides thereof. Moreover, the slit 17b can control insertion speed of the intraocular lens 1 to match advancement speed of the push rod 12.

Figure 18:
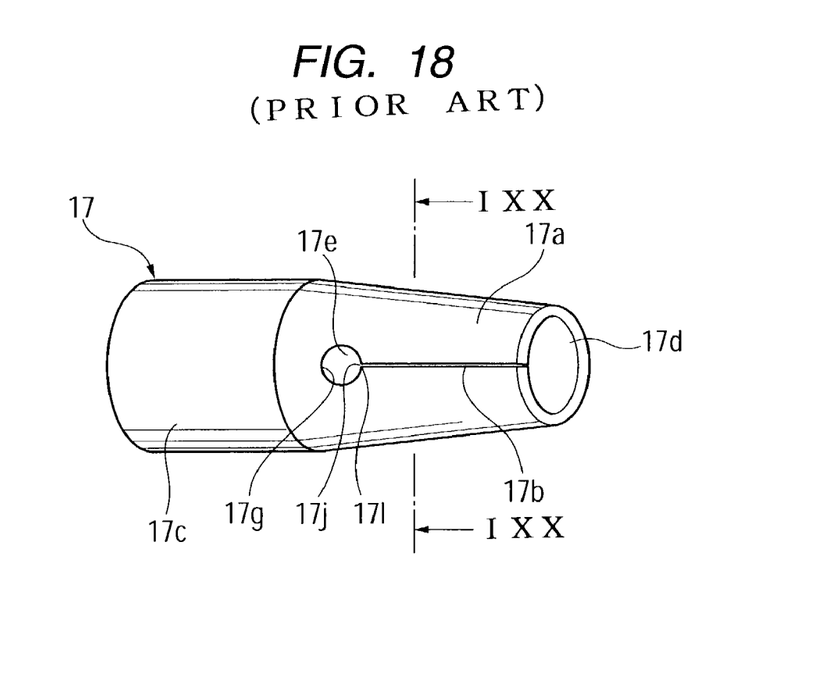
FIG. 18 is an enlarged perspective view of the insertion end portion of another conventional intraocular-lens insertion device.
Figure 19:
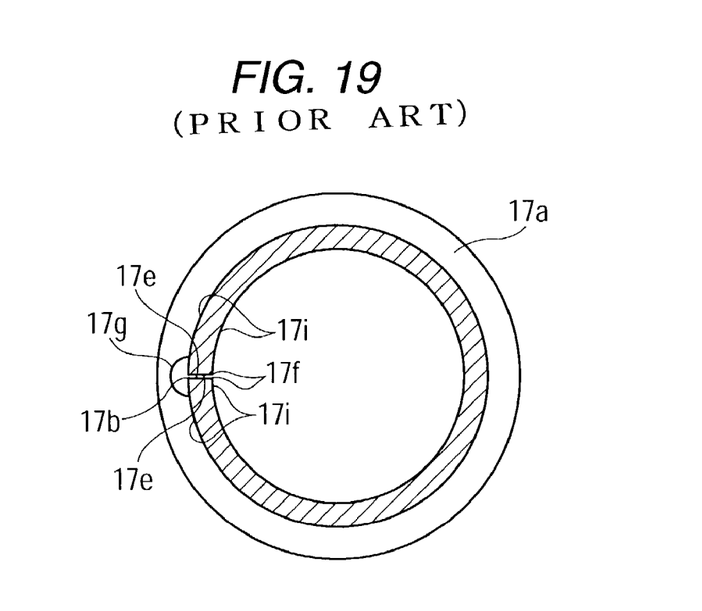
FIG. 19 is a cross sectional view taken along line IXX—IXX of FIG. 18.
Figure 20:
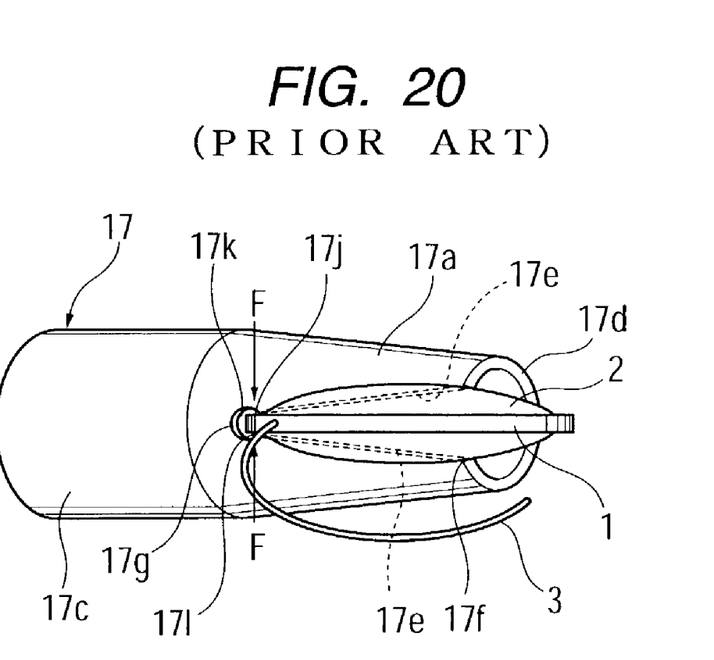
FIG. 20 is a view showing behavior of the insertion end portion of FIG. 18.

Moreover, there has been known an insertion device in which a slit and a hole are formed in the insertion end portion, as shown in FIGS. 18 to 20. A slit 17b is formed in the insertion end portion 17a in such a manner that no clearance is formed between upper and lower cut surfaces 17e of the slit 17b; i.e., the upper and lower cut surfaces 17e can come into contact with each other. Further, a hole 17g for crack prevention is formed in the insertion end portion 17a such that the hole 17g penetrates the wall of the insertion end portion 17a perpendicular to the axis thereof and provides an open portion 17k at a base-end-side end portion 17j of the slit 17b.

However, in the conventional intraocular-lens insertion device, the slit 17b formed in the tapered insertion end portion 17a of the insertion tube 17 has angular corners 17f which are formed between the upper and lower cut surfaces 17e and the inner and outer wall surfaces 17i of the insertion tube 17 and which extend along the axial direction. When the intraocular lens 1 is held within the slit 17b, the angular corners 17f are in contact with the opposite faces of the optical portion 2 of the intraocular lens 1 while biting thereinto. When the intraocular lens 1 is pushed out in this state, large frictional force is generated between their contact surfaces, thereby preventing smooth performance of the push-out operation.

Further, the slit 17b formed in the tapered insertion end portion 17a involves variation in terms of the shapes of angular inner and outer corner portions 17f and the cut surfaces 17e of the slit 17b stemming from errors arising during formation of the slit 17b, whereby pressing force acting on the contact surface of the optical portion 2 of the intraocular lens 1 changes at locations along the slit 17b, resulting in variation in nipping force produced by the slit 17b.

Moreover, due to the variation in nipping force produced by the slit 17*b*, anomalous friction force is generated between the cut surfaces 17*e* and the opposite faces of the optical portion 2 of the intraocular lens 1, whereby the operator experiences difficulty in maintaining stable lens insertion speed and controlling insertion speed with high reproducibility. Therefore, the insertion operation requires skill.

Furthermore, in the conventional insertion device in which the crack prevention hole 17*g* is formed at the end portion 17*j* of the slit 17*b*, as shown in FIG. 20, angular corner portions 17*l* are formed between the wall of the hole 17*g* and the cut surfaces 17*e* at the end portion 17*j* of the slit 17*b*. Therefore, the corner portions 17*l* apply large pressing force to a rear portion of the intraocular lens 1 in the directions of arrow F, so that a difference in nipping force is produced at the end portion 17*j* of the slit 17*b*, thereby preventing smooth control of the insertion speed of the intraocular lens.

SUMMARY OF THE INVENTION

In view of the foregoing, an object of the present invention is to provide an insertion device for a deformable intraocular lens in which uniform friction force is generated stably between opposite faces of an intraocular lens and cut surfaces of a slit formed in an insertion end portion of the insertion device, to thereby maintain constant lens insertion speed during an operation of inserting the intraocular lens into the eye.

In order to achieve the above-described object, the present invention provides an insertion device for deforming a deformable intraocular lens to a smaller size and inserting the intraocular lens into an eye via an insertion tube, wherein a slit is formed in an insertion end portion of the insertion tube, and cut surfaces of the slit and at least an inner wall surface of the insertion end portion are connected by curved surfaces. The slit may be formed in such a manner that the cut surfaces can come into contact with each other or are separated from each other by a predetermined distance. Preferably, curved surfaces are formed at only corner portions between the cut surfaces of the slit and at least inner wall surface of the insertion end portion. Preferably, the slit is formed in such a manner that inner and outer wall surfaces of the insertion end portion are smoothly connected by curved surfaces.

By virtue of the above-described configuration, the smoothly curved surfaces of the slit produce stable pressing force and stabilize frictional force, so that the intraocular lens can be smoothly inserted into the eye at a constant speed.

In the insertion device according to the present invention, a hole may be formed in the insertion end portion at an end of the slit in such a manner that corner portions are formed between the cut surfaces of the slit and a wall surface of the hole, the corner portions having a curved shape. This configuration can solve the conventional problem in that an intraocular lens held within the slit bites into the corner portions between the hole and the slit, whereby the intraocular lens is constrained. Thus, generation of unstable load can be prevented, and insertion speed of the intraocular lens can be controlled with ease, thereby facilitating surgical operation.

In the insertion device according to the present invention, a hole may be formed in the insertion end portion at an end of the slit, the slit being formed in such a manner that the distance between the cut surfaces gradually increases from an open end of the insertion end portion toward the hole and that the cut surfaces merge into a wall surface of the hole at diametrically opposite circumferential positions of the hole. This configuration can solve the conventional problem in that an intraocular lens held within the slit bites into the corner portions between the hole and the slit, whereby the intraocular lens is constrained. Thus, generation of unstable load can be prevented, and insertion speed of the intraocular lens can be controlled with ease, thereby facilitating surgical operation.

In the insertion device according to the present invention, the curved surfaces preferably are formed through pressing of a mirror-finished tool such that the curved surfaces each have an increased strength.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which:

FIGS. 5(1) AND 5(2) are cross sectional views taken along lines (V(1)—V(1) and V(2)—V(2) of FIG. 4;

DETAILED DESCRIPTION OF PREFERRED EMBODIMENTS

Embodiments of the present invention will be described with reference to the accompanying drawings.

First, an intraocular-lens insertion device according to a first embodiment of the present invention will be described with reference to FIGS. 1 to 7.

Figure 1:
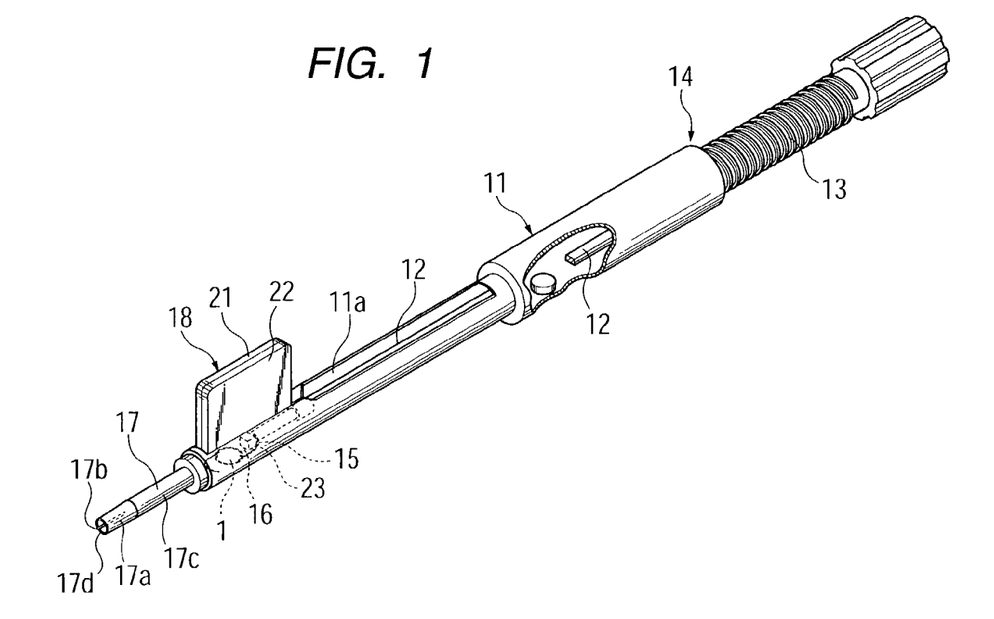
FIG. 1 is a partially cutaway perspective view of an intraocular-lens insertion device according to a first embodiment of the present invention.

As shown in FIG. 1, the intraocular-lens insertion device of the present embodiment includes a generally cylindrical, tubular device body 11; a push rod 12 fitted into the device body 11; a push-out mechanism 14 including a male-thread shaft 13 in screw-engagement with a female thread (not shown) formed on the inner wall surface of the device body 11; and an enclosing member 18, which has a lens receiving section 16 having a hinge portion 15, and an insertion tube 17 projecting forward from the lens receiving section 16. An attachment groove 11a is formed in an upper portion of a tip end portion of the device body 11 so to extend along the axial direction. The enclosing member 18 is loaded into the device body 11 via the groove 11a. The push rod 12 is rotatably connected to the male-thread shaft 13 and is supported by the device body 11 in such a manner that its rotation with respect to the device body 11 is restricted.

Figure 2:
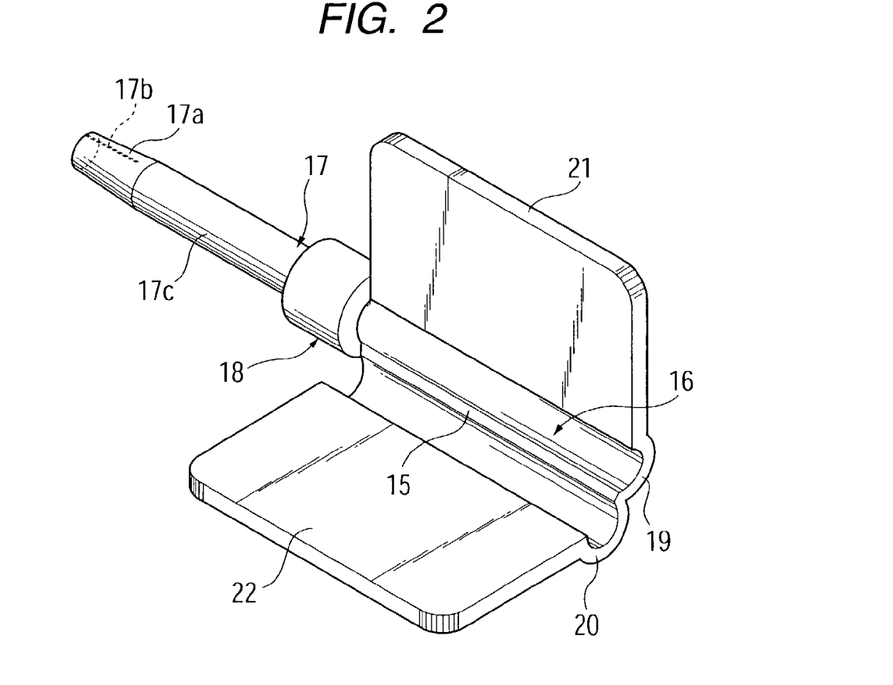
FIG. 2 is an enlarged perspective view of the enclosing member of FIG. 1.
Figure 3:
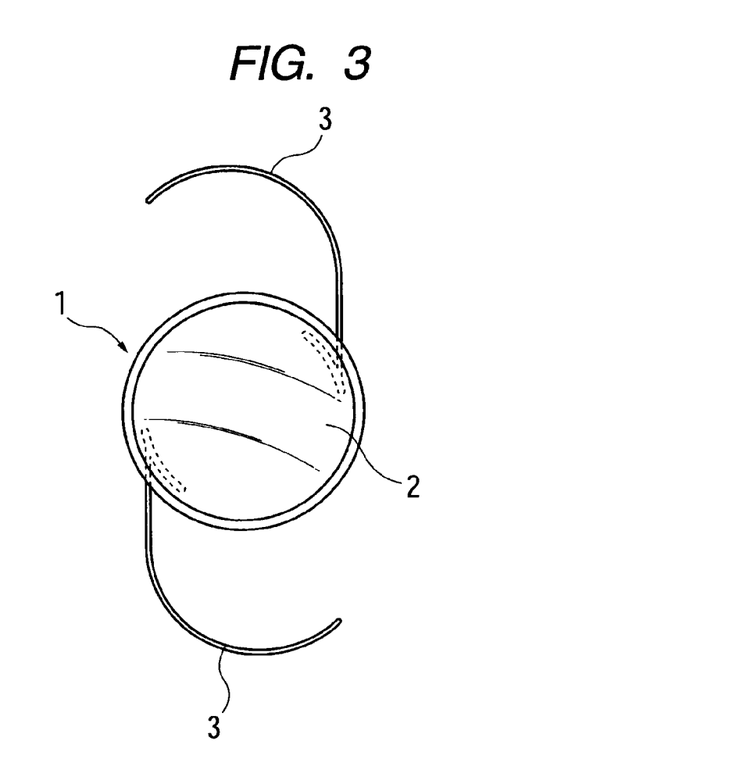
FIG. 3 is an enlarged plane view of a conventional deformable intraocular lens.
Figure 4:
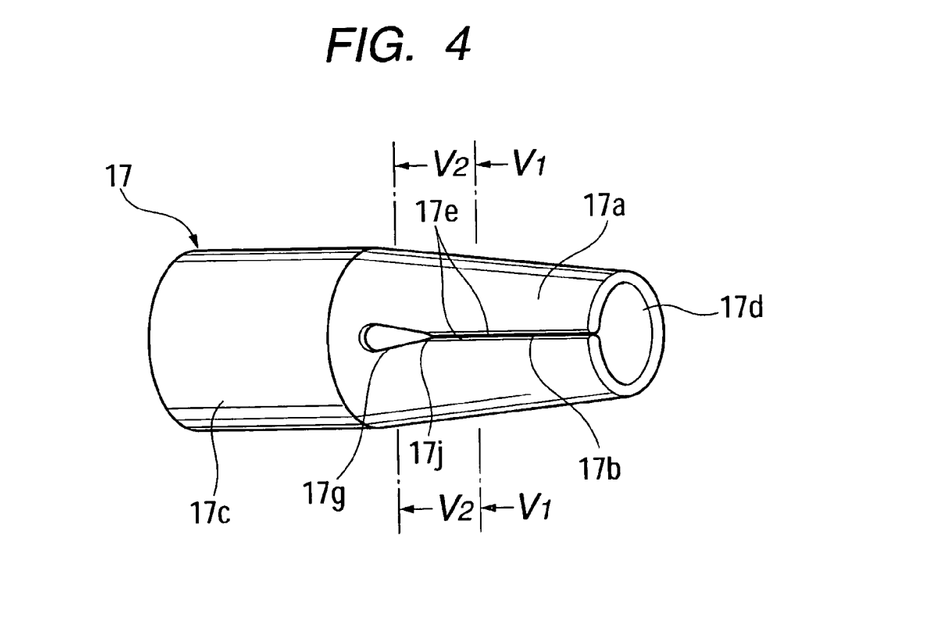
FIG. 4 is an enlarged perspective view of the insertion end portion of FIG. 1.
Figure 5:
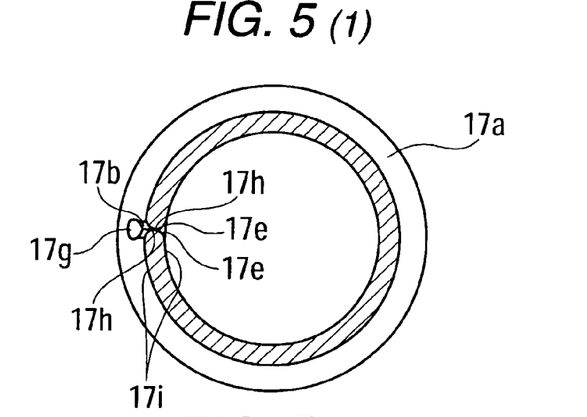

As shown FIG. 2, the lens receiving section 16 of the enclosing member 18 has a stationary half sleeve 19 and a movable half sleeve 20, whose lower edge portions are connected together by means of the hinge portion 15. The stationary half sleeve 19 is fixedly provided at the rear end of the insertion tube 17. The movable half sleeve 20 is located close to the rear end of the insertion tube 17 and can be opened and closed with respect to the stationary half sleeve 19. Stationary and movable press plates 21 and 22 project from the stationary and movable half sleeves 19 and 20, respectively.

The movable half sleeve 20, the hinge portion 15, and the movable press plate 22 constitute an open/close mechanism. When the open/close mechanism is closed, the movable press plate 22 comes into contact with the stationary press plate 21, so that the stationary half sleeve 19 and the movable half sleeve 20 form a tube that is coaxial with the insertion tube 17.

The insertion tube 17 has an internal diameter at its base end portion 17c which is equal to that of the tube which is formed by the stationary half sleeve 19 and the movable half sleeve 20 upon mutual contact. The insertion tube 17 has a tapered insertion end portion 17a which extends from the base end portion 17c.

The structure described above is substantially identical with that disclosed in Japanese Patent Application Laid-Open (kokai) No. 08-038542 (prior art).

As shown in FIGS. 4 to 7, the intraocular-lens insertion device according to the first embodiment has a slit 17b which is formed in the insertion end portion 17a. The slit 17b extends parallel to the axis of the insertion end portion 17a from the open end toward the base end portion and has a length shorter than a portion of the insertion end portion 17a which is to be inserted into the eye through an incision formed thereon. A hole 17g for crack prevention is formed at the end of the slit 17b located near the base end portion 17c. By means of continuous line machining, the hole 17g is formed to extend from the slit 17b.

Moreover, as best seen from an enlarged cross sectional views of FIGS. 5(1) and 5(2), the upper and lower cut surfaces 17e of the slit 17b are rounded into curved surfaces 17h. Reference numeral 17d denotes an open end of the insertion end portion 17a.

Further, the tip end portion 23 of the push rod 12 is formed to have a flattened transverse cross section; and curbed portions provided on the opposite sides of the tip end portion 23 come into contact with an inner wall surface of the insertion tube 17 excepting for the tapered insertion end portion 17a. The intraocular lens 1 shown in FIG. 3 has a circular optical portion 2 and two symmetrically disposed supports 3. The circular optical portion 2 is made of an elastic material having predetermined memory characteristics. The supports 3 are made of a material different from that of the optical portion 2.

The intraocular-lens insertion device according to the first embodiment having the above-described structure is used as follows. First, the enclosing member 18 is removed from the attachment groove 11a of the device body 11. Subsequently, the movable press plate 22 and the movable half sleeve 20 of the enclosing member 18 are opened; and the optical portion 2 of the intraocular lens 1 is placed on the hinge portion 15 of the lens receiving section 16 while a predetermined clearance is formed therebetween, such that one support 3 of the intraocular lens 1 is located on the front side and the other support 3 of the intraocular lens 1 is located on the rear side. Subsequently, the movable press plate 22 and the movable half sleeve 20 are closed and brought into contact with the stationary press plate 21 and the stationary half sleeve 19, respectively, whereby the optical portion 2 is folded in half within the half sleeves 19 and 20 to thereby be deformed to a smaller size. Subsequently, the enclosing member 18 is attached to the attachment groove 11a of the device body 11. After the insertion end portion 17a of the insertion tube 17 is inserted into an incision formed in the eye, the male-thread shaft 13 of the push-out mechanism 14 is rotated. As a result, the tip end portion 23 of the push rod 12 pushes the optical portion 2 of the intraocular lens 1 into the insertion end portion 17a of the insertion tube 17, whereby the intraocular lens 1 is gradually ejected into the eye while opening the slit 17b of the insertion end portion 17a.

Figure 6:
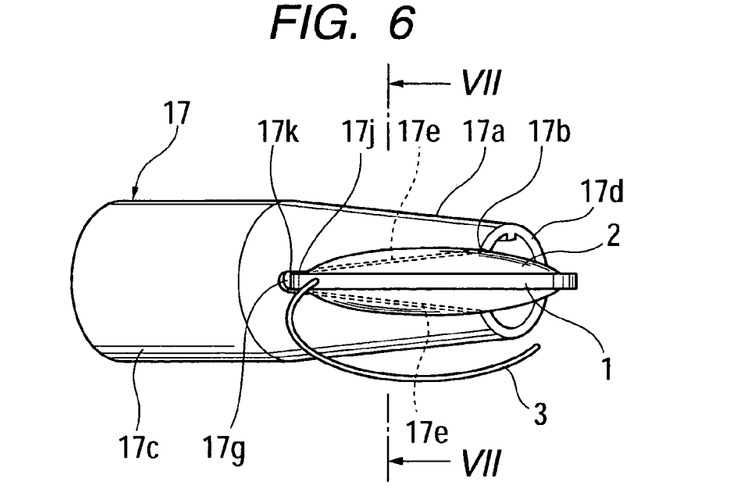
FIG. 6 is a perspective view of the insertion end portion which is used for describing operation of the device of FIG. 1.
Figure 7:
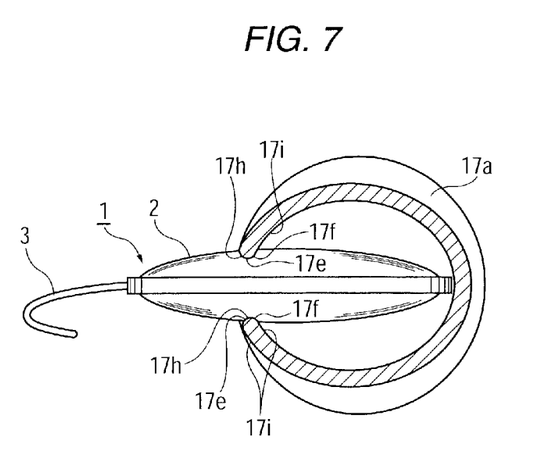
FIG. 7 is a cross sectional view taken along line VII—VII of FIG. 6.

When the intraocular lens 1 has arrived at the insertion end portion 17a, as shown in FIGS. 6 and 7, the intraocular lens 1 starts restoring its original shape. At this time, the optical portion 2 of the intraocular lens 1 is nipped between the curved surfaces 17h. After the intraocular lens 1 has substantially restored its original shape, the intraocular lens 1 is ejected from the open end 17d of the insertion end portion 17a.

Unlike the conventional insertion device, the corner portions 17f formed between the upper and lower cut surfaces 17e of the slit 17b and the inner and outer wall surfaces 17i of the insertion tube 17 are not angular; and the curved surfaces 17h come into contact with the opposite faces of the optical portion 2 of the intraocular lens 1. Therefore, stable frictional force can be maintained.

The slit 17b and the crack prevention hole 17g are formed by means of continuous machining in such a manner that no stepped portion (or sharp corner portion) is formed at boundaries between the end portion 17j of the slit 17b and the hole 17g. Since unnecessary restriction of the intraocular lens is removed when the intraocular lens 1 is pushed into the insertion end portion 17a and is thus allowed to restore its original shape, only the friction force generated by the curved surfaces 17h acts on the intraocular lens 1, so that insertion speed can be stabilized with ease.

Figure 8:
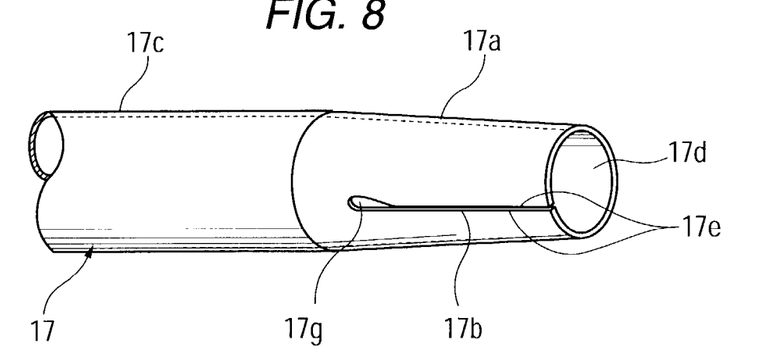
FIG. 8 is an enlarged perspective view of the insertion end portion showing a modification of the first embodiment.
Figure 9:
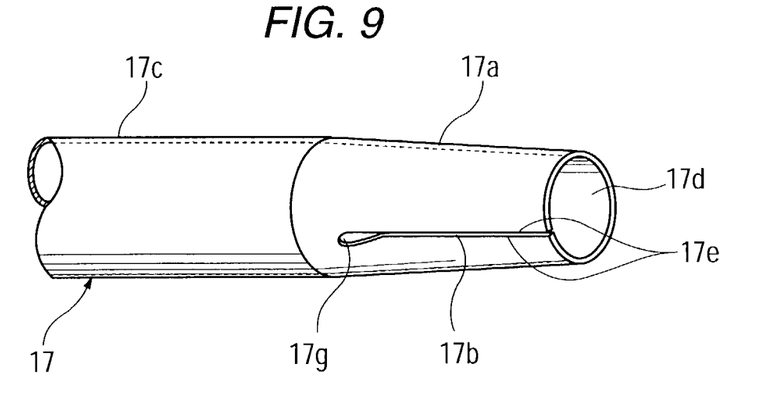
FIG. 9 is an enlarged perspective view of the insertion end portion showing another modification of the first embodiment.
Figure 10:
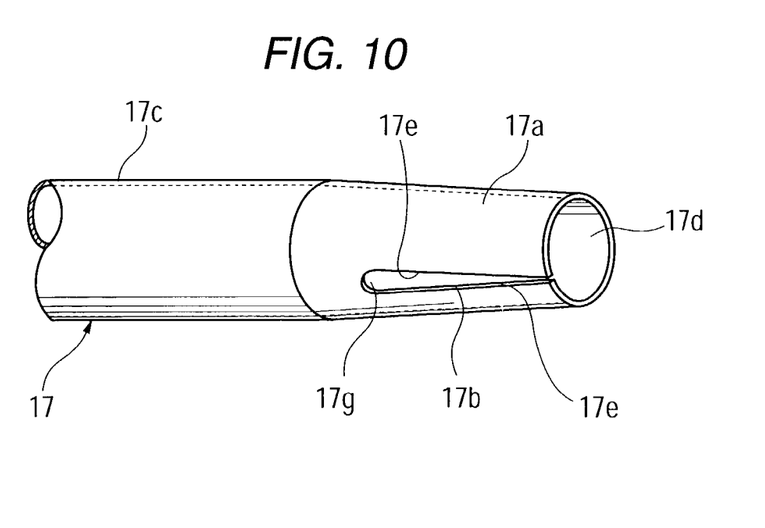
FIG. 10 is an enlarged perspective view of the insertion end portion showing still another modification of the first embodiment.

FIGS. 8, 9, and 10 show modifications of the slit 17b according to the first embodiment. In the modification shown in FIG. 8, a crack prevention hole 17g of a droplet shape is formed at the end portion 17j of the slit 17b by means of continuous machining in such a manner that the wall of the hole 17g is continuous from the cut surfaces 17e and the hole 17g deviates upward in FIG. 8.

In the modification shown in FIG. 9, a crack prevention hole 17g of a droplet shape is formed at the end portion 17j of the slit 17b by means of continuous machining in such a manner that the wall of the hole 17g is continuous from the cut surfaces 17e and the hole 17g deviates downward in FIG. 9.

In the modification shown in FIG. 10, a crack prevention hole 17g is formed at the end portion 17j of the slit 17b by means of continuous machining in such a manner that the distance H between the upper and lower cut surfaces 17e increases gradually from the open end 17d of the insertion end portion 17a toward the maximum radius positions of the hole 17g; i.e., diametrically opposite circumferential positions on the wall surface of the hole 17g.

The slits 17a of these modifications expectedly achieve the same effect as that achieved by the first embodiment.

Figure 11:
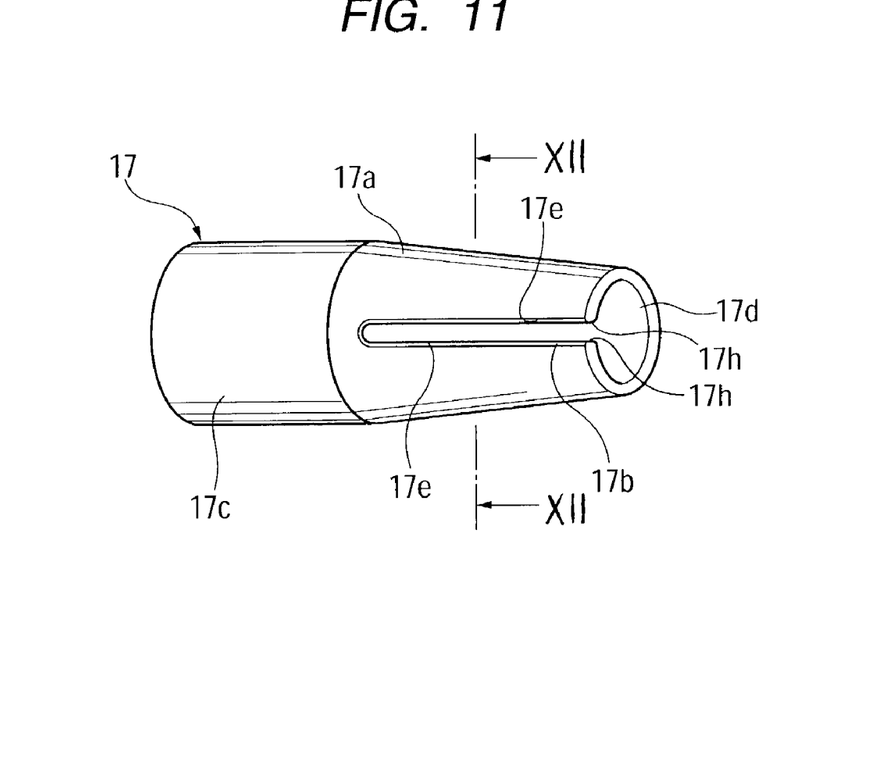
FIG. 11 is a perspective view of the insertion end portion of an intraocular-lens insertion device according to a second embodiment of the present invention.
Figure 12:
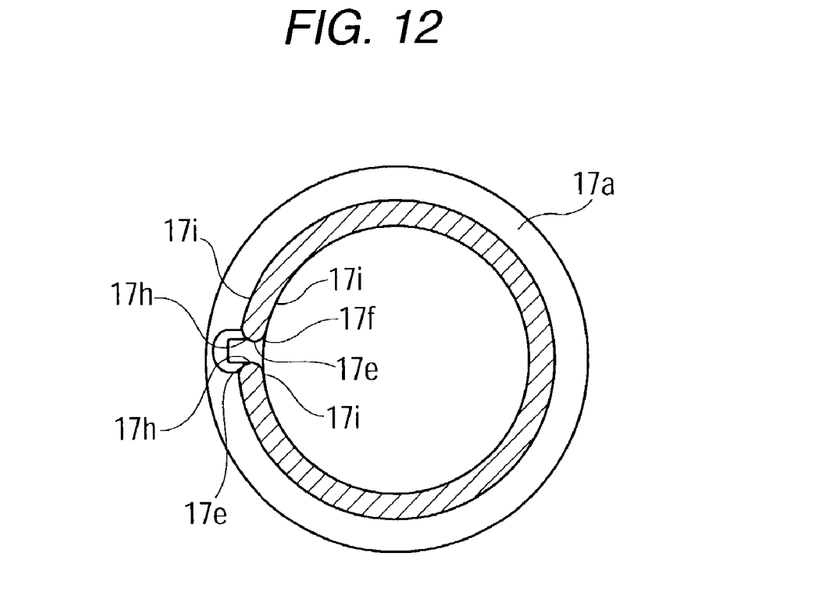
FIG. 12 is a cross sectional view taken along line XII—XII of FIG. 11.

Next, an insertion device according to a second embodiment of the present invention will be described with reference to FIGS. 11 and 12.

In the insertion device of the a second embodiment, the slit 17b is formed in the tapered insertion end portion 17a of the insertion tube 17 in such a manner that a clearance of a predetermined width H is formed between the upper and lower cut surfaces 17e; i.e., the slit 17a has a predetermined width H. The slit 17b has a length shorter than a portion of the tapered insertion end portion 17a which is to be inserted into the eye through an incision formed thereon. The width H of the slit 17b is slightly smaller than the thickness of an optical portion 2 of an intraocular lens 1. For example, when the optical portion 2 of the intraocular lens 1 has a thickness of 1 mm, the width H of the slit 17b is set to 0.9 mm. The upper and lower cut faces 17e of the slit 17b are formed into curved surfaces 17h in such a manner that the curved surfaces 17h are smoothly connected to the inner and outer wall surfaces 17i of the insertion tube 17.

Structural features other than the slit 17b are the same as those of the first embodiment. Therefore, these features are denoted by the same reference numerals, and their repeated description are omitted.

The insertion device according to the second embodiment achieves the same effects as those achieved by the first embodiment. The insertion device according to the second embodiment is suitable for intraocular lenses in which the lens portion has a relatively large thickness, in view that the width H of the slit 17b increases easily when the intraocular lens 1 is pushed out. In addition, the optical portion 2 can be held properly by means of the slit 17b, and insertion speed of the intraocular lens 1 can be controlled properly by means of controlling feed speed of the push rod 12.

In the first and second embodiments, curved surfaces are preferably formed to cover boundaries between the cut surfaces of the slit 17b and the inner and outer wall surfaces of the insertion tube 17. However, curved surfaces may be formed to cover only boundaries between the cut surfaces of the slit 17b and the inner wall surface of the insertion tube 17, with which an intraocular lens first comes into contact.

Next, a method of forming the slit in the intraocular-lens insertion device of the present invention will be described.

In the case in which the insertion tube 17 is molded by means of injection molding, and the slit 17b is formed in the insertion end portion 17a of the insertion tube 17 by feeding a cutting tool from the open end 17d along the axis of the base end portion 17c in such a manner that the upper and lower cut surfaces 17e of the slit 17b come into contact with each other, a machining tool (not shown) having mirror-finished opposite faces is inserted between the upper and lower cut surfaces 17e of the slit 17b, and pressing force is applied to the tool and/or the insertion end portion 17a to thereby finish the corner portions 17f of the upper and lower cut surfaces 17e into curved shapes. According to this machining method, the strength of the material in the vicinity of the cut surfaces 17e and the corner portions 17f is increased, whereby damage to or breakage of the insertion end portion 17a and the slit 17b can be prevented.

In the above-described case, alternatively, a heated pin-shaped tool having a mirror-finished surface and a small diameter is pressed against the axially extending corner portions 17f between the cut surfaces 17e and the inner and outer circumferential walls 17i of the insertion tube 17, whereby the corner portions are fused and formed to have smoothly curved surfaces.

In the case in which the slit 17b is formed in the insertion end portion 17a of the insertion tube 17 to have a predetermined width H, the insertion tube 17 is accommodated within a bottle containing glass beads, and the bottle is tumbled for a predetermined period of time. As a result, glass beads enter the slit 17b and hit the cut surfaces 17e and the corner portions 17f, whereby smoothly curved surfaces are formed thereon. Alternatively, the corner portions 17f may be subjected to electropolishing.

Alternatively, a heated cutting tool is fed into the insertion end portion 17a of the injection-molded insertion tube 17 from the open end 17d along the axis of the base end potion 17c to thereby form the slit 17b. Since cutting and melding are performed simultaneously, smoothly curved surfaces can be formed without formation of angular corner portions in the slit 17b.

Moreover, the slit may be formed through melting and cutting by use of a laser beam. In this case as well, the same effect can be attained.

Obviously, numerous modifications and variations of the present invention are possible in light of the above teachings. It is therefore to be understood that within the scope of the appended claims, the present invention may be practiced otherwise than as specifically described herein.

What is claimed is:

1. An intraocular-lens insertion device for deforming a deformable intraocular lens to a smaller size and inserting the intraocular lens into an eye via an insertion tube, said insertion tube having an axially extending slit in an insertion end portion of the insertion tube, said slit having cut surfaces, and edges joining cut surfaces of the slit and at least an inner wall surface of the insertion end portion comprising convex curved corners, said device further comprising a hole in the insertion end portion at an end of the slit, the distance between the cut surfaces gradually increasing from an open end of the insertion end portion toward the hole, the cut surfaces merging into a wall surface of the hole at diametrically opposite circumferential positions of the hole.

* * * * *